United States Patent [19]

Petit et al.

[11] Patent Number: 5,972,827
[45] Date of Patent: Oct. 26, 1999

[54] CATALYTIC OXYCHLORINATION OF HYDROCARBONS TO PRODUCE CHLOROCARBONS

[75] Inventors: Alain Petit, Martigues; Roland Bachelard, Lyons; Rene Clair, Martigues; Yves Correia, Chateau-Arnoux, all of France

[73] Assignee: Atochem, Paris la Defense Cedex, France

[21] Appl. No.: 08/035,076

[22] Filed: Mar. 22, 1993

Related U.S. Application Data

[62] Division of application No. 07/990,939, Dec. 14, 1992, Pat. No. 5,243,111, which is a continuation of application No. 07/720,642, Jun. 25, 1991, abandoned.

[30] Foreign Application Priority Data

Jun. 25, 1990 [FR] France .................................. 90 07932

[51] Int. Cl.$^6$ ........................... B01J 27/122; B01J 21/08; B01J 23/70
[52] U.S. Cl. ......................... 502/225; 502/244; 502/345; 502/346; 502/355
[58] Field of Search ..................... 502/225, 244, 502/345, 346, 355

[56] References Cited

U.S. PATENT DOCUMENTS 4,339,620   7/1982   Cowfer et al. .......................... 570/243
5,053,567  10/1991   Correia et al. ...................... 502/225 X

FOREIGN PATENT DOCUMENTS 0278922   8/1988   European Pat. Off. .
997825    7/1965   United Kingdom .
1271776   4/1972   United Kingdom .
1474258   5/1977   United Kingdom .

*Primary Examiner*—Walter D. Griffin
*Attorney, Agent, or Firm*—Burns, Doane, Swecker & Mathis, L.L.P.

[57] ABSTRACT

Hydrocarbons, e.g., ethylene, are steady-state catalytically oxychlorinated into chlorocarbons, e.g., 1,2-dichloroethane, by fluidizing a fluidizable charge by directing a gaseous feedstream containing a hydrocarbon therethrough and therein oxychlorinating such hydrocarbon, the gaseous feedstream further comprising an oxygen-containing gas and gaseous hydrochloric acid and the fluidizable charge comprising immixture of a catalytically effective amount of an oxychlorination catalyst and particles of a catalytically and chemically inert solid substance, and which further comprises introducing a solution or suspension of a catalytically active copper compound into such fluidized charge during the oxychlorination reaction.

12 Claims, No Drawings

CATALYTIC OXYCHLORINATION OF HYDROCARBONS TO PRODUCE CHLOROCARBONS

This application is a divisional of application Ser. No. 07/990,939, filed Dec. 14, 1992 (now U.S. Pat. No. 5,243,111), which is a continuation of Ser. No. 07/720,642, filed Jun. 25, 1991 (now abandoned).

BACKGROUND OF THE INVENTION

The present invention relates to an oxychlorination process and catalyst for the production of chlorocarbons, especially 1,2-dichloroethane.

DESCRIPTION OF THE PRIOR ART 1,2-Dichloroethane (D 12) is a compound manufactured industrially on a scale of several million tons per year, which, on pyrolysis, is converted into vinyl chloride monomer (VCM) and hydrochloric acid (HCl). VCM is polymerized into poly(vinyl chloride) (or PVC), a widely used polymer. The HCl produced on pyrolysis is separated from the VCM and is then contacted with ethylene and oxygen in the presence of a catalyst to produce D 12; this is the oxychlorination reaction. Such reaction is very general and can be carried out employing the majority of hydrocarbons.

The oxychlorination reaction is abundantly described in the patent literature, in particular in FR 2,063,365, FR 2,260,551, FR 2,213,259 and FR 2,125,748. The catalyst is characteristically a copper salt deposited onto alumina powder.

EP 58,644 describes the preparation of an oxychlorination catalyst, comprising pouring a solution of cupric chloride into a fluidized bed of alumina powder and at a maximum temperature of 50° C. This operation is followed by drying with hot air in a fluidized bed and at a temperature not exceeding 140° C.

EP 29,143 describes the preparation of an oxychlorination catalyst by mixing, in a fluidized bed during an oxychlorination reaction, a catalyst which is already prepared, namely, alumina powder containing a copper compound, with naked support material, namely, alumina powder devoid of any copper compound. A supplementary addition of the naked support material to a fluidized bed during an oxychlorination reaction, originally charged with catalyst, is also described.

This technique is described as presenting the advantage of avoiding the adhesion (or agglomeration) of catalyst particles during the operation. EP 29,143 also describes a migration of the copper compound from the alumina containing the copper towards the naked support. It is apparent that the result of this technique is a reduction in the copper content of the catalyst, since the amount of support is increased without compensating amounts of copper being added. This is evidence that the "suppression or reduction of adhesion" is not associated only with the reduction in the amount of copper but also with the migration of the copper compound from the alumina containing the copper compound to the naked support.

The '143 application also describes the preparation of the catalyst in situ by charging the reactor with naked support, fluidizing it with the reaction gases and adding solid cupric chloride thereto. This is suggested as a substitute for the conventional preparation of the catalyst by impregnation external to the reactor. However, this preparation is suggested only on the laboratory scale; indeed, such method of preparation is not industrial, because at the beginning of the preparation the fluidized bed does not contain any catalyst proper, i.e., copper compound deposited onto a support. Therefore, no oxychlorination reaction is then carried out and it is necessary to heat the reaction mixture and, if heating is applied while no catalyst thus exists at the outlet of the fluidized bed there is an explosive region, since there is no reaction and therefore no conversion.

EP 119,933 also describes an oxychlorination catalyst according to the same principle as above, i.e., copper impregnating an alumina powder, but not having the disadvantage of adhering because, as is stated, there is less copper at the surface than within the catalyst particles.

The aforesaid prior art relates to oxychlorination fluidized beds employing a "homogeneous" catalyst, namely, powders in which all of the particles are impregnated with copper.

There also exist oxychlorination fluidized beds employing a "heterogeneous" catalyst, i.e., powders comprising a mixture of alumina particles impregnated with copper as above and inert particles such as siliceous sand. These catalysts are described in FR 2,242,143, hereby expressly incorporated by reference. These "heterogeneous" catalysts do not exhibit the disadvantage of adhesion of the "homogeneous" catalysts, but, on the other hand, present the disadvantage of forming a self-abrasive mixture; the sand particles result in the wear of the alumina particles. Copper-rich fines are removed and fresh catalyst must be added to compensate therefor.

SUMMARY OF THE INVENTION

Accordingly, a major object of the present invention is the provision of an improved "heterogeneous" oxychlorination process/catalyst wherein the performance of the catalyst is maintained constant over time.

To prevent confusion with the usual terms of homogeneous catalysis and heterogeneous catalysis and to remain consistent with the terms of FR 2,242,143, the "heterogeneous" oxychlorination catalysts will herein be designated a fluidizable charge or fluidizable catalytic charge.

Briefly, the present invention features the oxychlorination of a hydrocarbon to form a chlorinated hydrocarbon, in which the hydrocarbon, a gas containing oxygen and gaseous hydrochloric acid are conveyed through a fluidizable charge comprising a mixture of an oxychlorination catalyst and particles of at least one catalytically and chemically inert solid substance, and further wherein a solution or a suspension of a copper compound is incrementally added to the fluidized charge over the course of the reaction.

The present invention also features such catalyst compositions, per se.

DETAILED DESCRIPTION OF THE PREFERRED EMBODIMENTS OF THE INVENTION

More particularly according to the present invention, the subject oxychlorination catalysts comprise a mixture of an oxychlorination catalyst and of particles of at least one catalytically and chemically inert solid substance to which a solution or a suspension of a copper compound has been added.

The hydrocarbon may be pure or may be a mixture of a plurality of hydrocarbons selected from among $C_1$–$C_{20}$ aliphatic hydrocarbons, cycloaliphatic hydrocarbons up to $C_{12}$ and aromatic hydrocarbons containing up to 4 condensed benzene nuclei, and chlorinated derivatives thereof.

Exemplary such hydrocarbons include methane, ethane, propane, ethylene and propylene. The invention is particularly applicable for the oxychlorination of ethylene.

The gas containing oxygen can simply be air, but it can also be employed depleted or enriched in oxygen.

The oxychlorination catalysts which can be employed in the invention may be any oxychlorination catalyst capable of being employed, per se, without being admixed with a catalytically and chemically inert substance. Powders based essentially on alumina of a particle size ranging from 20 to 200 $\mu$m and having a specific surface area ranging from 90 to 450 $m^2/g$ and preferably from 30 to 90 $\mu$m and from 250 to 400 $m^2/g$ are advantageously used. These powders are impregnated with copper or a copper salt in an amount which may be up to 10% and preferably from 3% to 10% by weight of copper relative to the catalyst final product.

Exemplary catalytically and chemically inert substances serving as a diluent (but in no event as a catalyst support), particularly representative are glass or silica, ballotini, alpha alumina and, preferably, siliceous sand which is available in the natural state and whose particle size distribution is adapted to the requirements of the fluidization.

The particle size distribution of the actual catalyst, on the one hand, and that of the catalytically and chemically inert substance, on the other, are selected such that the diameter and the particle size range of the mixture promote satisfactory fluidization.

The size of the inert particles advantageously ranges from 20 to 200 $\mu$m.

The amount of inert substance may vary over wide limits. The amount of such inerts advantageously ranges from 1 to 20 times by weight of the amount of catalyst.

The objective of the oxychlorination is essentially to employ hydrochloric acid as the source of chlorine. The amount of oxygen and of hydrocarbon is therefore adjusted to provide the chlorinated hydrocarbon approximately stoichiometrically by consuming as much HCl and hydrocarbon as possible.

During oxychlorination in a fluidized bed, a decrease in catalytic activity typically results, reflected by a reduced conversion of the hydrocarbon.

This decrease is due to catalyst wear. Such wear, which results in a decrease in activity, is accompanied by a physical loss of catalyst fines by entrainment with the gases at the outlet of the fluidized bed and an imperfect efficiency of the means of separation between the entrained catalyst and the gases. This separation is rendered difficult by the conversion of a fraction of the catalyst into dust because of attrition. The reduction in the amount of catalyst and the decrease in its activity are generally compensated for by additions of fresh catalyst.

However, it has now unexpectedly and surprisingly been found that this decrease in activity can be offset/compensated for by incrementally adding a solution or a suspension of a copper compound to the fluidized bed. Among such copper compounds, the chloride and the oxychloride are particularly representative. It is preferred to add cupric chloride.

The formulation can be a suspension rather than a solution, if the concentration of the copper compound is high or if the copper compound is but slightly soluble.

The solution of the copper compound may be an aqueous solution. The solution or suspension is added to the oxychlorination reactor either continuously or discontinuously, but over the course of the oxychlorination procedure. It may be introduced via a spray nozzle.

The amount of copper to be introduced in solution form is a function of the performance which is required. The operation may be repeated as many times as necessary. In addition to this solution of a copper compound, it is also possible to add powdered copper, a powdered copper compound or fresh catalyst containing copper.

The copper or a powdered copper compound may be in the form of catalyst which is very rich in copper. By "very rich in copper" is intended that its content, expressed as copper as a weight percentage of the finished catalyst, is higher than that of the catalyst in use in the fluidized charge. This value is advantageously 1.2 times and preferably ranges from 1.5 to 3 times that of the catalyst contained in the fluidized charge.

For example, if the catalyst in use in the fluidized charge contains from 3.5% to 7% by weight of copper, catalyst additions are made containing approximately 12% by weight of copper. It is considered that this content of 12%, expressed as copper, is very rich in copper. In addition, it is an unusual value, because the process of providing it is much more complicated than in the case of the usual values of 3% to 8%.

The invention also features the above catalytic compositions or fluidizable charges, per se.

One advantage of the invention, when compared with the traditional operation which entails compensating for the decrease in activity and the decrease in the amount of catalyst only by additions of fresh catalyst, is steadier running where activity surges are avoided, and the improvement is more long-lived.

In order to further illustrate the present invention and the advantages thereof, the following specific examples are given, it being understood that same are intended only as illustrative and in nowise limitative.

EXAMPLE 1

(1) Test No. 1: Procedure Carried out Under Operating Conditions not in Accordance with the Invention In a reactor 3 m in diameter, producing 25 tons/h of 1,2-dichloroethane, a fluidized bed was established and the operating conditions were the following:
Temperature: 245 to 250° C.
Pressure: 4 bars
Residence time: 25 to 30 sec
Catalyst system: 8 tons of alumina impregnated to a concentration of 5% of copper (catalyst) plus silica (22) tons. The alumina had a specific surface area of 357 $m^2/g$, a mean diameter of 53 $\mu$m, a pore volume of 33 $cm^3/100$ g and a packing density of 1,192 $kg/m^3$. The silica was a Fontainebleau sand (pure silica) having a mean diameter of 50 $\mu$m and a particle size distribution ranging from 20 to 300 $\mu$m.

The results obtained are reported in the Table below.

(2) Test No. 2: Procedure Carried out According to the Invention with Additions of a Solution of Cupric Chloride to the Catalyst Bed The procedure of Test No. 1 was repeated, under the same conditions, except that a solution of cupric chloride was periodically added thereto. Discontinuous additions were made, corresponding to amounts of copper metal of 50 to 200 kg. The results obtained are also reported in the Table below:

TABLE

| | $\frac{HCl}{C_2H_4}$ (mole mole) | $\frac{O_2}{C_2H_4}$ (mole mole) | $Y_G$ (%) Degree of conversion of HCl | $X_{D12}$ (%) Degree of conversion into D12 | R $C_2H_4$ (%) Degree of conversion into chlorinated products | Exhaust (volume %) | | | | Catalyst consumption* (g/t D12) | Cu (wt. % of the bed) | Cu consumption** (g/t D12) |
|---|---|---|---|---|---|---|---|---|---|---|---|---|
| | | | | | | $C_2H_4$ | $CO_2$ | CO | $O_2$ | | | |
| Test No. 1 | 1.97 | 0.68 | 99.5 | 95.5 | 96.8 | 0.42 | 1.20 | 0.60 | 5 | 250 | 1 to 1.2 | 0 |
| Test No. 2 | 1.99 | 0.63 | 99 | 96 | 97.3 | 0.30 | 1.00 | 0.65 | 4.25 | 120 | 2.5 to 3 | 25 |

*The catalyst consumption reflects the additions of catalyst which were identical to the catalyst constituting the initial catalytic system (catalyst + silica)
**The copper consumption is a consumption of cupric chloride in solution, expressed as metallic copper.

The catalyst consumption and consumption of cupric chloride solution, expressed in grams per ton of D 12 manufactured, are reported in the Table. The additions of catalyst and of cupric chloride solution were carried out to provide uniform operating conditions.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An oxychlorination catalyst composition comprising immixture of (a) a catalytically effective amount of an oxychlorination catalyst, (b) a diluent comprising particles of a catalytically and chemically inert solid substance, which diluent is present in an amount ranging from 1 to 20 times by weight of the oxychlorination catalyst (a), and (c) a solution or suspension of a catalytically active copper compound.

2. The composition as defined by claim 1, said oxychlorination catalyst comprising an alumina powder impregnated with copper values.

3. The composition as defined by claim 2, such impregnated powder having a particle size ranging from 20 to 200 μm and a specific surface area ranging from 90 to 450 m²/g.

4. The composition as defined by claim 2, such impregnated powder comprising from 3% to 10% by weight of copper values.

5. The composition as defined by claim 2, such values comprising copper or a copper salt.

6. The composition as defined by claim 1, such inert particulates comprising glass, silica, ballotini, alumina, or siliceous sand.

7. The composition as defined by claim 6, such inert particulates having a particle size ranging from 20 to 200 μm.

8. The composition as defined by claim 1, said catalytically active copper compound comprising copper chloride or copper oxychloride.

9. The composition as defined by claim 1, said catalytically active copper compound comprising copper chloride.

10. The composition as defined by claim 2, said solution or suspension of a catalytically active copper compound further comprises an additional catalyst which is very rich in copper.

11. The composition as defined by claim 10 wherein the copper content of the additional catalyst is from 1.5 to 3 times the copper content of the oxychlorination catalyst of (a).

12. In an oxychlorination process catalyst composition wherein the improvement comprises the inclusion of (i) a diluent comprising particles of a catalytically and chemically inert solid substance which is present in an amount ranging from 1 to 20 times by weight of the oxychlorination catalyst and (ii) a solution or suspension of a catalytically reactive copper compound.

* * * * *